(12) United States Patent
Andresen et al.

(10) Patent No.: US 11,938,321 B2
(45) Date of Patent: Mar. 26, 2024

(54) ANTENNA ASSEMBLY FOR SUPPLYING POWER TO AN IMPLANTABLE NEURAL STIMULATOR DEVICE

(71) Applicant: Curonix LLC, Pompano Beach, FL (US)

(72) Inventors: Chad David Andresen, Miami Beach, FL (US); Richard LeBaron, Miami Beach, FL (US); Laura Tyler Perryman, Pompano Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 0 days.

(21) Appl. No.: 18/090,591

(22) Filed: Dec. 29, 2022

(65) Prior Publication Data

US 2023/0277847 A1 Sep. 7, 2023

Related U.S. Application Data

(63) Continuation of application No. 16/536,380, filed on Aug. 9, 2019, now Pat. No. 11,541,238, which is a
(Continued)

(51) Int. Cl.
*A61N 1/36* (2006.01)
*A61N 1/372* (2006.01)
*A61N 1/378* (2006.01)

(52) U.S. Cl.
CPC ....... *A61N 1/36125* (2013.01); *A61N 1/3605* (2013.01); *A61N 1/37229* (2013.01); *A61N 1/3787* (2013.01)

(58) Field of Classification Search
CPC .............. A61N 1/36125; A61N 1/3605; A61N 1/37229; A61N 1/3787
See application file for complete search history.

(56) References Cited

U.S. PATENT DOCUMENTS 7,760,152 B2   7/2010  Seppa
10,058,705 B2  8/2018  Andresen
(Continued)

FOREIGN PATENT DOCUMENTS

WO   WO 2012/138782   10/2012
WO   WO 2013/019757    2/2013
(Continued)

OTHER PUBLICATIONS

Extended European Search Report in European Application No. 15876382.1, dated Jul. 10, 2018, 12 pages.
(Continued)

*Primary Examiner* — Ankit D Tejani
*Assistant Examiner* — Joshua Brendon Solomon
(74) *Attorney, Agent, or Firm* — Maschoff Brennan

(57) ABSTRACT

An antenna assembly includes a metal layer configured to emit linearly polarized electromagnetic energy to a receiving antenna implanted underneath a subject's skin; and a feed port configured to connect the antenna assembly to a signal generator such that the antenna assembly receives an input signal from the signal generator and then transmits the input signal to the receiving dipole antenna, wherein the antenna assembly is less than 200 um in thickness, and wherein the metal layer is operable as a dipole antenna with a reflection ratio of at least 6 dB, the reflection ratio corresponding to a ratio of a transmission power of the antenna assembly in transmitting the input signal and a reflection power seen by the antenna assembly resulting from electromagnetic emission of the input signal.

20 Claims, 22 Drawing Sheets

Related U.S. Application Data continuation of application No. 16/019,094, filed on Jun. 26, 2018, now Pat. No. 10,426,960, which is a continuation of application No. 14/986,324, filed on Dec. 31, 2015, now Pat. No. 10,058,705.

(60) Provisional application No. 62/098,946, filed on Dec. 31, 2014.

(56) References Cited

U.S. PATENT DOCUMENTS

| | | | |
|---|---|---|---|
| 10,426,960 B2 | 10/2019 | Andersen et al. | |
| 11,541,238 B2 | 1/2023 | Andersen et al. | |
| 2007/0058686 A1 | 3/2007 | Capasso et al. | |
| 2008/0304686 A1 | 12/2008 | Meskens et al. | |
| 2009/0192381 A1 | 7/2009 | Brockway et al. | |
| 2010/0171675 A1 | 7/2010 | Borja et al. | |
| 2011/0009926 A1 | 1/2011 | Lin | |
| 2011/0250402 A1 | 10/2011 | Oldham et al. | |
| 2012/0004708 A1* | 1/2012 | Chen | A61N 1/37223 607/60 |
| 2012/0111950 A1 | 5/2012 | Worrall | |
| 2012/0203130 A1 | 8/2012 | Bernhard | |
| 2012/0212380 A1 | 8/2012 | Theobold | |
| 2012/0281957 A1 | 11/2012 | Maysamreza et al. | |
| 2013/0056689 A1 | 3/2013 | Zhang et al. | |
| 2013/0066400 A1* | 3/2013 | Perryman | A61N 1/37229 607/59 |
| 2013/0088304 A1 | 4/2013 | Henderson et al. | |
| 2013/0310901 A1 | 11/2013 | Perryman et al. | |
| 2014/0275847 A1 | 9/2014 | Andersen et al. | |
| 2014/0336727 A1 | 11/2014 | Perryman et al. | |
| 2014/0371802 A1 | 12/2014 | Mashiach et al. | |
| 2015/0028805 A1 | 1/2015 | Dearden et al. | |

FOREIGN PATENT DOCUMENTS

| | | |
|---|---|---|
| WO | WO 2013/025632 | 2/2013 |
| WO | WO 2013/040549 | 3/2013 |
| WO | WO 2012/103519 | 3/2014 |
| WO | WO 2014/153219 | 9/2014 |
| WO | WO 2014/153223 | 9/2014 |
| WO | WO 2014/153228 | 9/2014 |

OTHER PUBLICATIONS

Extended European Search Report in European Appln No. 21177219. 9, dated Nov. 30, 2021, 6 pages.

International Search Report and Written Opinion in International Application No. PCT/US2015/68348, dated Mar. 17, 2016, 18 pages.

PCT International Preliminary Report on Patentability in International Appln. No. PCT/US2015/068348, dated Jul. 12, 2017, 10 pages.

* cited by examiner

ANTENNA ASSEMBLY FOR SUPPLYING POWER TO AN IMPLANTABLE NEURAL STIMULATOR DEVICE

CROSS REFERENCE TO RELATED APPLICATIONS

This application is a continuation of U.S. application Ser. No. 16/536,380, filed Aug. 9, 2019, which is a continuation of U.S. application Ser. No. 16/019,094, filed Jun. 26, 2018, now U.S. Pat. No. 10,426,960, issued Oct. 1, 2019, which is a continuation of U.S. application Ser. No. 14/986,324, filed Dec. 31, 2015, now U.S. Pat. No. 10,058,705, issued Aug. 28, 2018, which claims the benefit of U.S. provisional Patent Application 62/098,946, titled ANTENNA ASSEMBLY, and filed on Dec. 31, 2014. All of these prior applications are incorporated by reference in their entirety.

TECHNICAL FIELD

This application relates generally to an antenna assembly to couple energy to an implanted stimulator device.

BACKGROUND

Modulation of excitable tissue in the body by electrical stimulation has become an important type of therapy for patients with chronic disabling conditions, including pain, movement initiation and control, involuntary movements, vascular insufficiency, heart arrhythmias and various other modalities. A variety of therapeutic intra-body electrical stimulation techniques can be utilized to provide therapeutic relief for these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

SUMMARY

In one aspect, some implementations provide an antenna assembly that includes: a metal layer configured to emit linearly polarized electromagnetic energy to a receiving antenna implanted underneath a subject's skin; and a feed port configured to connect the antenna assembly to a signal generator such that the antenna assembly receives an input signal from the signal generator and then transmits the input signal to the receiving dipole antenna, wherein the antenna assembly is less than 200 um in thickness, and wherein the metal layer is operable as a dipole antenna with a reflection ratio of at least 6 dB, the reflection ratio corresponding to a ratio of a transmission power of the antenna assembly in transmitting the input signal and a reflection power seen by the antenna assembly resulting from electromagnetic emission of the input signal.

Implementations may include one or more of the following features.

The metal layer may be shaped as a rectangle, and wherein a long axis of the rectangle may align with a direction of the linear polarization of the electromagnetic energy. The metal layer may include four rounded fillets. The metal layer may be a two-leaf structure that includes two leaves each having three vertices, wherein the two leaves may adjoin each other at one vertex, and wherein the remaining vertices of each leaf may be rounded as fillets. The metal layer may be operable to create a higher electric field than a metal layer configured as other than the two-leaf structure while maintaining a surface area identical to the two-leaf structure. The feed port may be located at the vertex where the two leaves adjoin each other.

The antenna assembly may be configured such that the antenna assembly can be bent up to 50 degrees while maintaining the reflection ratio of more than 6 dB. The antenna assembly may be configured to emit transcranially the linearly polarized electromagnetic energy when the antenna assembly is worn as an ear piece. The antenna assembly may configured to emit the linearly polarized electromagnetic energy to a receiving antenna implanted up to 6 cm underneath a subject's skin. The antenna assembly may be configured such that the reflection ratio of at least 6 dB is maintained regardless of a separation between the metal layer and a subject's skin. The antenna assembly may be configured such that the reflection ratio of at least 6 dB is maintained with an air gap and without gel coupling between the metal layer and the subject's skin. The antenna assembly may be configured to operate with a quality factor (Q) no more than 9. The antenna assembly may be configured to operate at a frequency between 800 MHz and 3 GHz.

In another aspect, some implementations provide a system that includes a signal generator configured to generate an input signal containing electrical energy and stimulation pulse parameters, an antenna assembly coupled to the signal generator and configured to receive an input signal from the signal generator and then transmit the same to a receiving dipole antenna of a passive stimulator device implanted underneath the subject's skin such that the antenna assembly operates with a reflection ratio of at least 6 dB, the reflection ratio corresponding to a ratio of a transmission power of the antenna assembly in transmitting the input signal and a reflection power seen by the antenna assembly resulting from electromagnetic emission of the input signal, the antenna assembly including: a feed port configured to connect the antenna assembly to the signal generator such that the antenna assembly receives the input signal from the signal generator; and a metal layer less than 200 um in thickness and configured to emit linearly polarized electromagnetic energy via radiative coupling to the receiving dipole antenna such that the passive stimulator device extracts the electrical energy from the input signal and then uses the extracted energy to create stimulation pulses suitable for stimulating tissue; and a passive neural stimulator device configured to be implanted underneath the subject's skin, the passive neural stimulator device including: a receiving dipole antenna configured to receive the input signal emitted from the antenna assembly; and circuitry coupled to the receiving dipole antenna, the circuitry being configured to: extract electric energy contained in the input signal; and use the extracted electrical energy to create stimulation pulses suitable for stimulating neural tissue, the stimulation pulses being created according to the stimulation pulse parameters.

Implementations may include one or more of the following features.

The antenna assembly may be configured to emit the linearly polarized electromagnetic energy to the receiving antenna implanted 1-3 cm underneath a subject's skin. The metal layer may be shaped as a rectangle, and wherein a long axis of the rectangle may align with a direction of the linear polarization. The metal layer may include a two-leaf structure that includes two leaves each having three vertices, wherein the two leaves adjoins each other at one vertex, and wherein the remaining vertices of each leaf are rounded as fillets. The feed port may be located on the adjoining vertex.

The antenna assembly may be configured such that the antenna assembly can be to be bent up to 50 degrees while maintaining the reflection ratio of more than 6 dB. The antenna assembly may be configured such that the reflection ratio of at least 6 dB is maintained with an air gap and without gel coupling between the metal layer and the subject's skin.

The details of one or more implementations are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
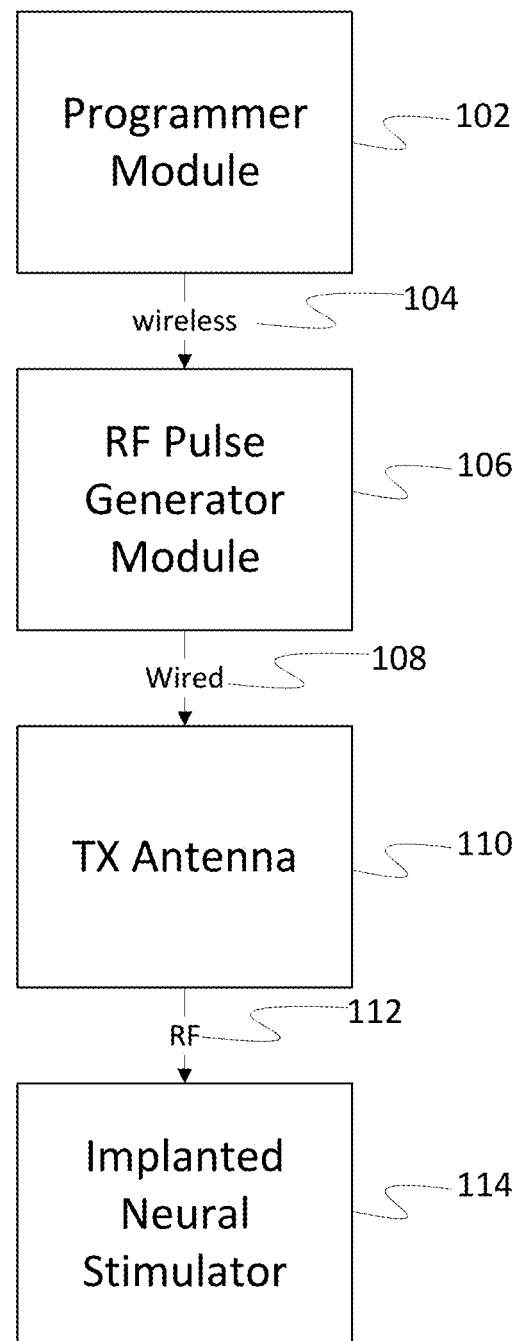
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power an implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

In some implementations, a signal generator and an antenna assembly may be configured as wearable by a subject. The signal generator may generate an input signal containing electrical energy and stimulation pulse parameters. The antenna assembly may be coupled to the signal generator, for example, through a feed port, to receive the input signal. The antenna assembly may be thin and flexible. For example, the antenna assembly may be less than 200 µm in thickness, and may be able to be bent up to 50 degrees while remaining operational. In some implementations, when the antenna assembly is worn by a subject, a metal layer of the antenna assembly faces the subject. This metal layer may be configured to emit linearly polarized electromagnetic energy to a receiving dipole antenna of a passive wireless stimulator device such that the wireless stimulator device extracts the electrical energy from the input signal and then uses the extracted energy to create stimulation pulses suitable for stimulating tissue. The metal layer may be shaped as a rectangle, much like a wide dipole antenna described herein. In this case, the long axis of the rectangular shape is aligned with the polarization direction. The metal layer may also be a two-leaf structure that includes two leaves adjoining each other at a vertex. In this case, the two leaves may operate as a signal arm and a ground arm at a given time. An axial direction of the leaves connecting the two arms may correspond to the direction of the linear polarization. In either case, the antenna assembly may be configured to emit the linearly polarized electromagnetic energy efficiently. For example, the antenna assembly may operate with a reflection ratio of at least 6 dB at an operating frequency of the antenna assembly. The reflection ratio corresponds to a ratio of a transmission power used by the antenna assembly to transmit the input signal and a reflection power seen by the antenna assembly resulting from electromagnetic emission of the input signal. The reflection ratio of at least 6 dB at an operating frequency of the antenna assembly may be maintained regardless of a separation between the metal layer and the subject's skin. For example, the antenna assembly may be configured such that reflection ratio of at least 6 dB at the operating frequency of the antenna assembly is maintained when the antenna assembly is between zero to 2 centimeters, or more particularly, between zero to 1 centimeter, away from the patient's skin.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
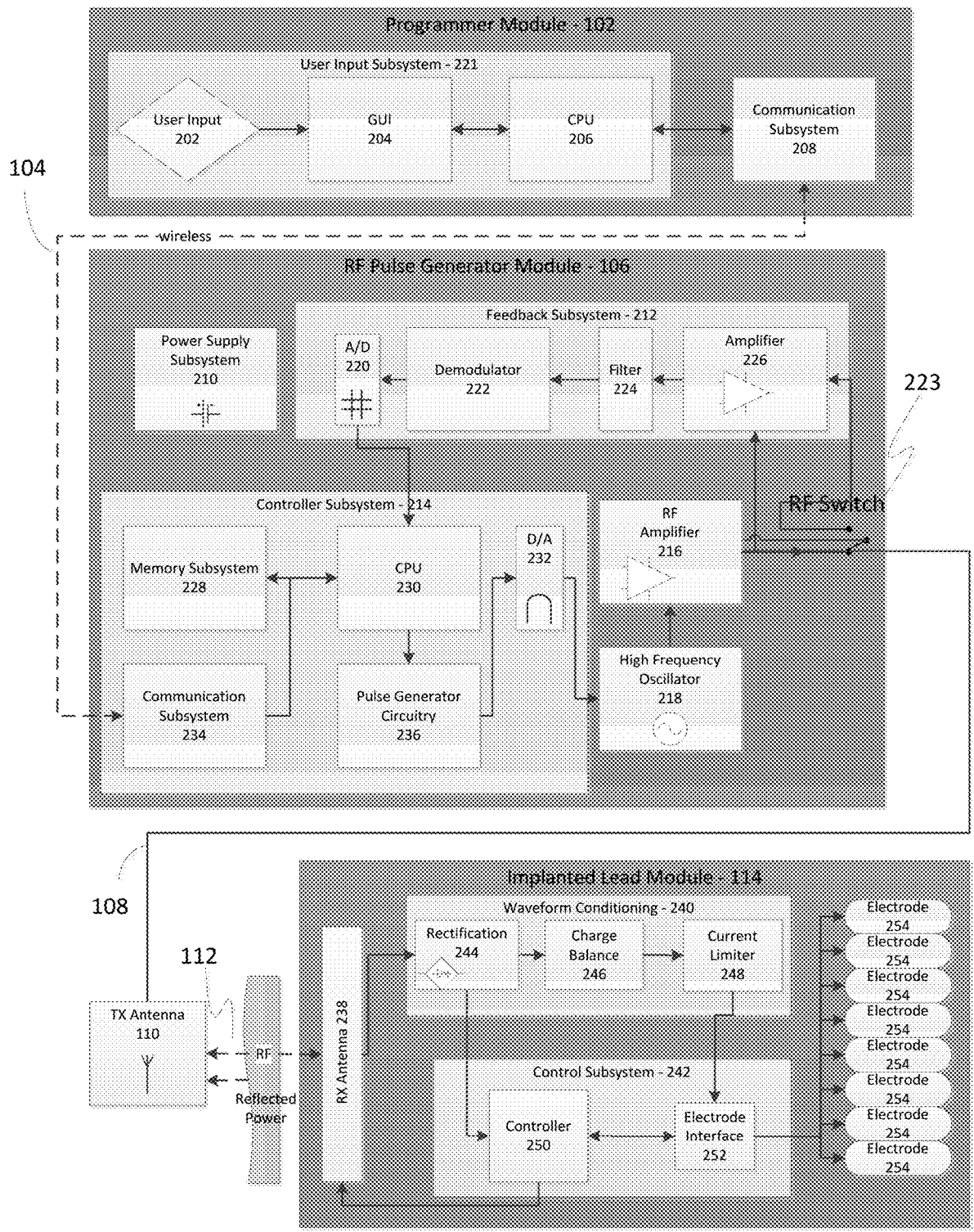
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
|---|---|
| Pulse Amplitude: | 0 to 25 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuro-anatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A delivered a stimulus phase, for example, 3 mA current for a duration of 200 microseconds followed by a 400 microseconds charge-balancing phase. This stimulus cycle, for example, could be specified to repeat at a rate of 60 cycles per second. Then, for set B, the controller 250 could specify a stimulus phase of 1 mA current for duration of 500 microseconds, followed by a 800 microseconds charge-balancing phase. The repetition rate for the set-B stimulus cycle can be set independently of set A, say for example, could be specified at 25 cycles per second. Or, if the controller 250 was configured to match the repetition rate for set B to that of set A, for such a case, the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm$^2$. In order to avoid the irreversible electrochemical reactions such as pH change, electrode dissolution as well as tissue destruction, no net charge should appear at the electrode-electrolyte interface, and it is generally acceptable to have a charge density less than 30 uC/cm$^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3:
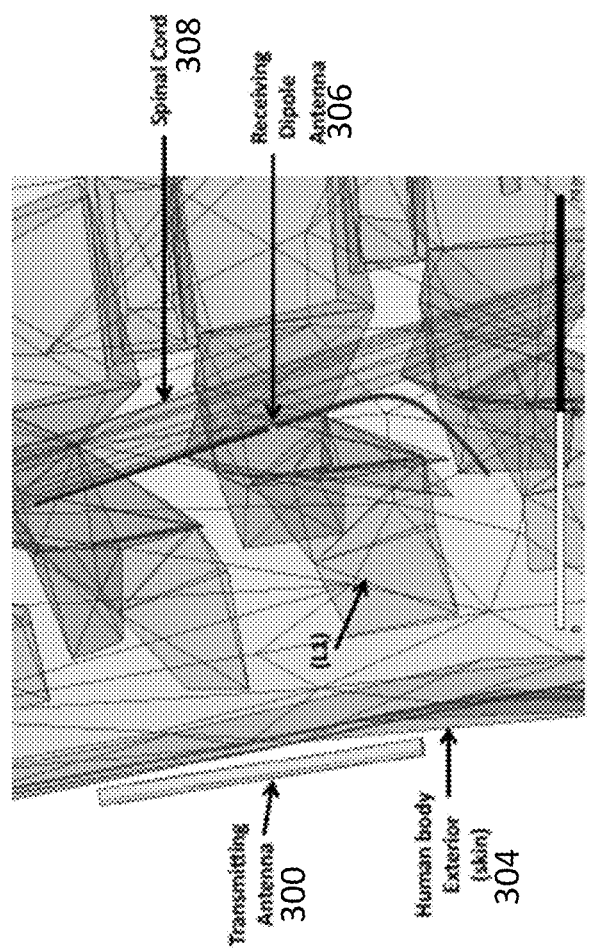
FIG. 3 illustrates a transmitting antenna coupling electromagnetic energy to a receiving dipole antenna through human skin, according to a simulation model.

FIG. 3 illustrates a transmitting antenna 302 coupling electromagnetic energy to a receiving dipole antenna 306 through a subject's skin 304. In particular, FIG. 3 illustrates the transmitting antenna 302 and its placement when the transmitting antenna 302 is transmitting to a receiving dipole antenna 306 of a stimulator device that is implanted under the skin 304. In this disclosure, transmitting antenna 302 refers to the assembly of components on a device that interact with an out-bound electromagnetic wave. In this example, the receiving dipole antenna 306 is part of a stimulator device implanted close to spinal cord 308 for stimulation thereof. Configurations may vary, for example, in separation distance from the transmitting antenna 302 to the skin 304 as well as the depth of the receiving dipole antenna 306 into the human body. In some configurations, the transmitting antenna 302 may be separated from the skin 304 by a distance of as short as 2 mm. In some examples, the depth of the receiving dipole antenna 306 may be up to 6 cm below the skin 304. Transmitting antenna 202 can accommodate for variances in separation distances when transmitting antenna 302 is judiciously configured to mitigate attenuation caused by longer distances. Such configurations may generally include size, shape, and polarization configurations. These configurations may include thin and flexible antenna assemblies. For example, the antenna assembly may be less than 200 μm in thickness. The antenna assembly may be bent up to 50 degrees while remaining operational in that the reflection ratio is maintained at 6 dB or better at the operating frequency of the antenna assembly.

In some instances, simulations may be performed to model the coupling of electromagnetic energy from the transmitting antenna assembly to a receiving dipole, for example, via radiative coupling. In one such example, as illustrated in FIG. 3 the antenna is located in proximity to the spinal cord centered in the vertebrae at Li. Simulations may be run with an ANSYS HFSS human body model. The receiving dipole antenna 306, realistically curved, is highlighted. Some implementations allow for thin and flexible transmitting antenna configurations that suit the overall ergonomics as a wearable medical device. For example, the antenna configurations of these implementations are comfortable to wear and easy to conceal when worn by a subject.

As discussed below, in some implementations, the transmitting antenna 302 is configured as a wide dipole antenna assembly while in some other implementations the antenna assembly is configured as bowtie antenna assembly. In either case, the antenna assembly may be configured to emit the linearly polarized electromagnetic energy efficiently. For example, the antenna assembly may operate with a reflection ratio of at least 6 dB at an operating frequency of the antenna assembly. The reflection ratio corresponds to a ratio of a transmission power used by the antenna assembly to transmit the input signal and a reflection power seen by the antenna assembly resulting from electromagnetic emission of the input signal. The reflection ratio of at least 6 dB may be maintained regardless of a separation between the metal layer and the subject's skin. Notably, the antenna assembly may be configured to emit, without direct contact with the subject's skin, the linearly polarized electromagnetic energy to the receiving dipole antenna. The emission is accomplished with an air gap between the antenna assembly and the subject's skin and without gel coupling between the metal layer and the subject's skin. The efficient transmission may have a broadband characteristic in that the antenna assembly is configured to operate with a quality factor (Q) no more than 9.

Figure 4A:
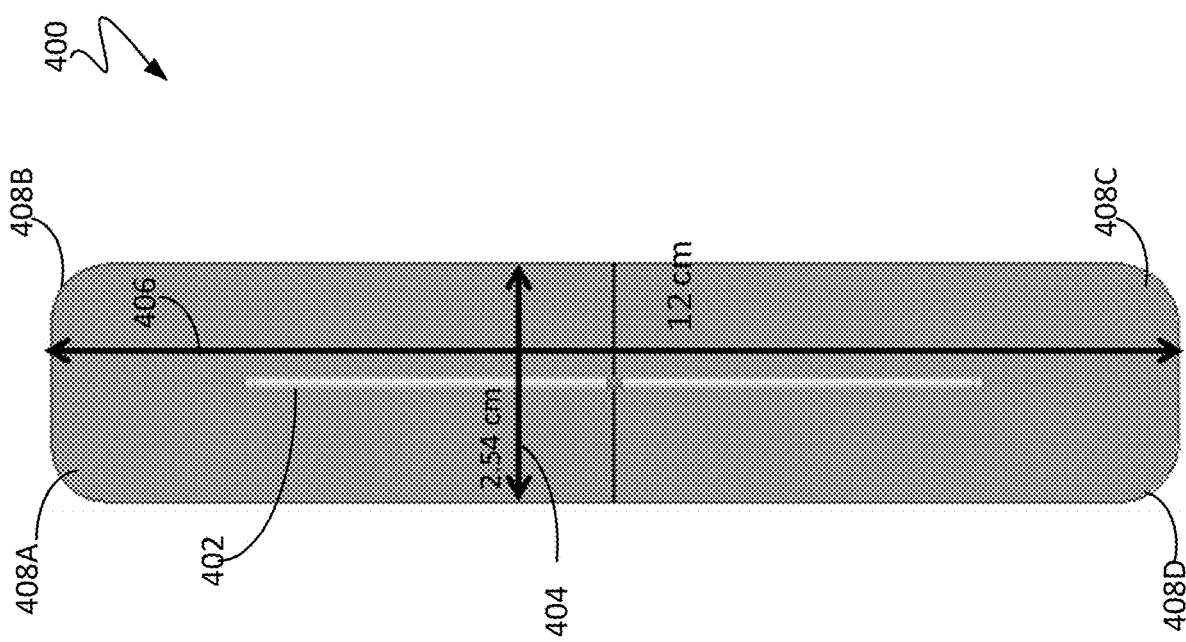
FIGS. 4A-4B show an example of a transmitting antenna configured as a wide dipole antenna assembly for operation at 915 MHz.
Figure 4B:
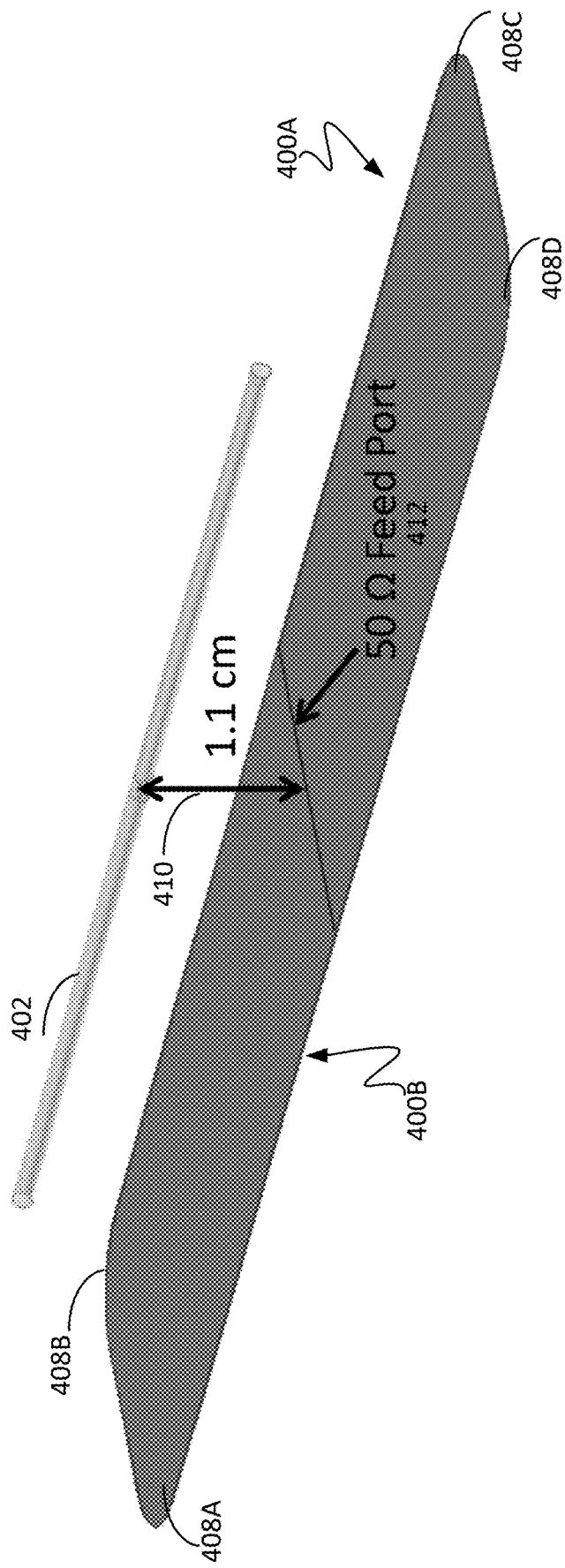

FIGS. 4A-4B show an example of transmitting antenna 302 configured as a wide dipole antenna assembly 400 for operation at 915 MHz. As illustrated, wide dipole antenna assembly 400 is generally rectangular in shape with a length 406 in the range of 4 cm to 20 cm, a width 404 of 1 cm to 5 cm and four rounded corners or fillets 408A to 408B. The particular example shown has a length of 12 cm and a width of 2.54 cm. As shown in FIG. 4B, the wide dipole antenna assembly 400 includes an inward surface 400A to radiate EM energy towards the implanted stimulator device underneath the skin. Inward surface 400A may be placed in close proximity to the skin surface of a human patient. Outward surface 400B may provide protection against mechanical wear and tear. FIG. 4B further shows 50Ω feed port 412, for connecting wide dipole antenna assembly 400 to, for example, a signal generator such as RF pulse generator module 106. This 50Ω feed port 412 may be at the midline of the outward surface 400B. By way of example, BNC (Bonet Neill-Concelman) or SMC (SubMiniature version A) type connectors can be used to connect 50 Q feed port 412 to an MFS device through a co-axial cable.

FIGS. 4A and 4B also show a receiving dipole antenna 402 relative to the wide dipole antenna assembly 400. As illustrated, the wide dipole antenna assembly 400 can be located 1 cm to 3 cm (410) from the receiving antenna 402. Wide dipole antenna assembly 400 radiates EM energy into the human body via the two ends along a longitudinal axis of metal layer. In particular, the wide dipole antenna 400 has one end formed by corners 408A and 408B, and another end formed by corners 408C and 408D. The two ends may form a dipole configuration capable of transmitting electromagnetic waves linearly polarized along the direction of the two ends. When coupling to the receiving dipole antenna 402, this linear polarization of antenna assembly is aligned with the long axis of receiving dipole antenna 402. In some configurations, the metal layer is as small as 20 to 200 μm in thickness.

Figure 5:
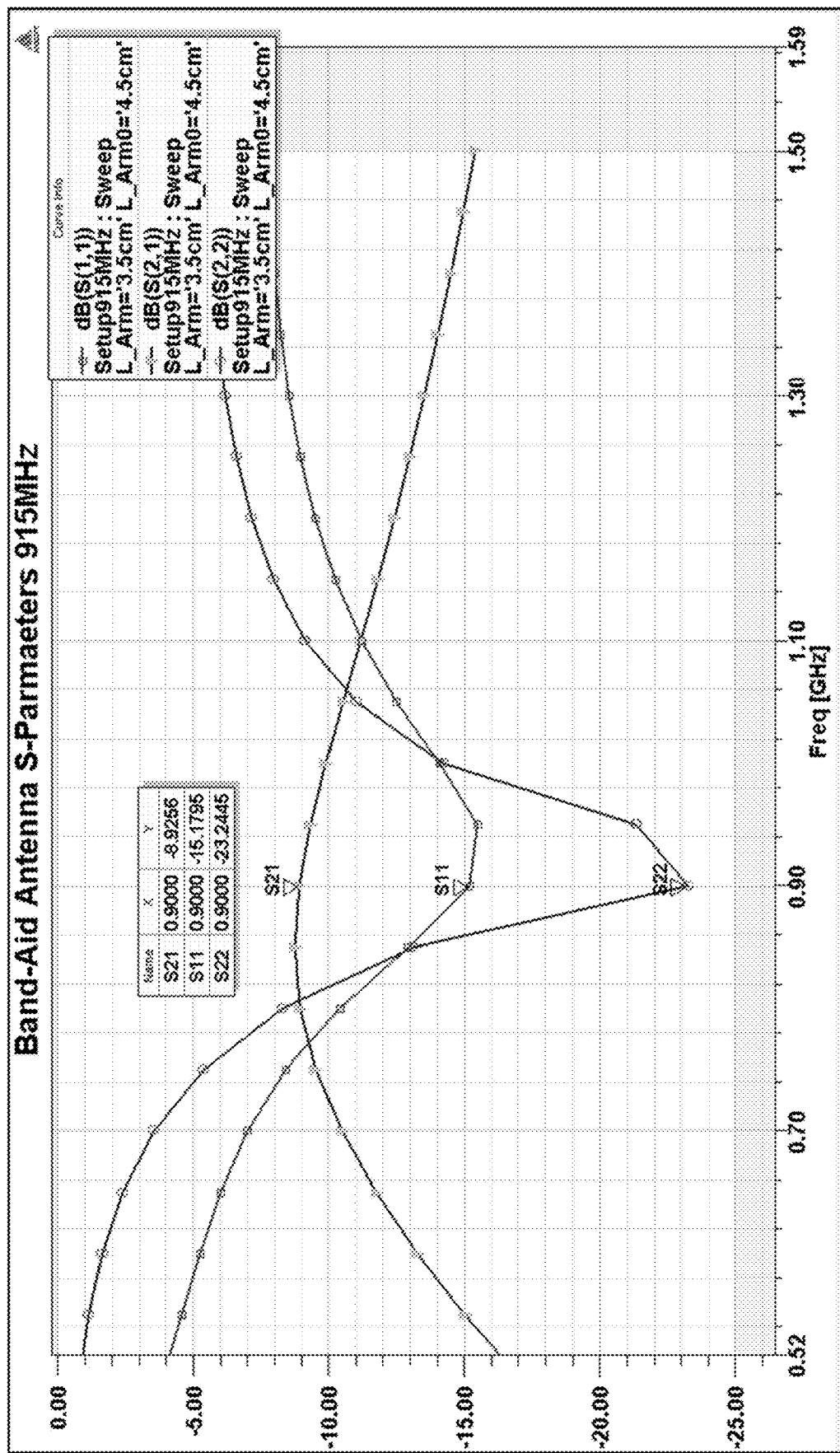
FIG. 5 shows S-parameter results of the wide dipole antenna assembly of FIGS. 4A-4B.
Figure 9:
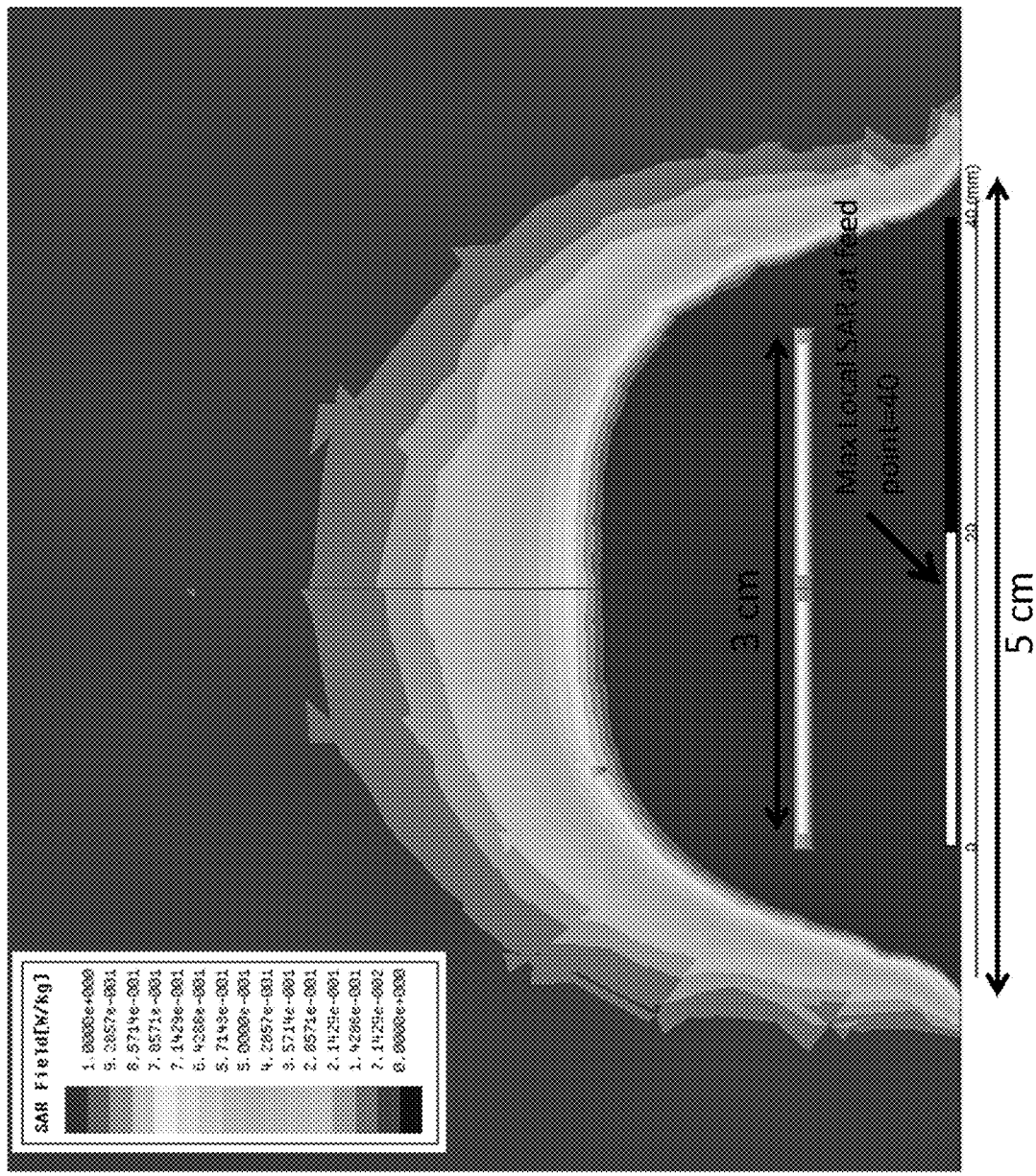
FIG. 9 shows example radiation patterns of the wide dipole antenna assembly of FIGS. 7A-7B.

FIG. 5 shows example S-parameter results of the wide dipole antenna assembly 400. Here, the S11 parameter (input port voltage reflection coefficient) and S22 parameter (output port voltage reflection coefficient) both have notches at the operating frequency of 915 MHz. Moreover, the S22 parameter is approximately 8 dB or so lower than the S11 parameter. These resonance performances are achieved without compromising the S21 parameter, which is the forward voltage gain. Notably, as shown in FIG. 9, the S11 parameter is under −10 dB at the operating frequency and, more specifically, is approximately −15.5 dB at the operating frequency. Accordingly, the wide dipole antenna assembly 400 is configured to operate with a reflection ratio of at least 10 dB. The reflection ratio corresponds to a ratio of the transmission power used by the wide dipole antenna assembly to emit the linearly polarized electromagnetic energy and the reflection power seen by the wide dipole antenna assembly resulting from electromagnetic emission using the transmission power. The transmission power represents the power level used by the transmitting antenna—wide dipole antenna assembly 400—in emitting linearly polarized electromagnetic energy so that the input signal containing electrical energy is sent to the receiving antenna on the implantable stimulator device. Meanwhile, the reflection power refers to the reflected power back to the RF source from the antenna—wide dipole antenna assembly 400. A 15 dB or more suppression means about 3% of the transmitted energy may get reflected. In other words, about 97% of the transmitted energy passes through. The antenna assembly 400 may be configured such that the reflection ratio of at least 10 dB at the operating frequency of the antenna assembly is maintained when the antenna assembly is positioned between zero to 2 centimeters, or more particularly, between zero to 1 centimeter, away from the patient's skin. That is, the antenna assembly 400 may be configured such that the S11 parameter notch at the operating frequency is wide enough that the S11 parameter remains below −10 dB as the antenna assembly 400 is positioned between 0 to 2 centimeters, or more particularly, between zero to 1 centimeter, away from the patient's skin.

Figure 6A:
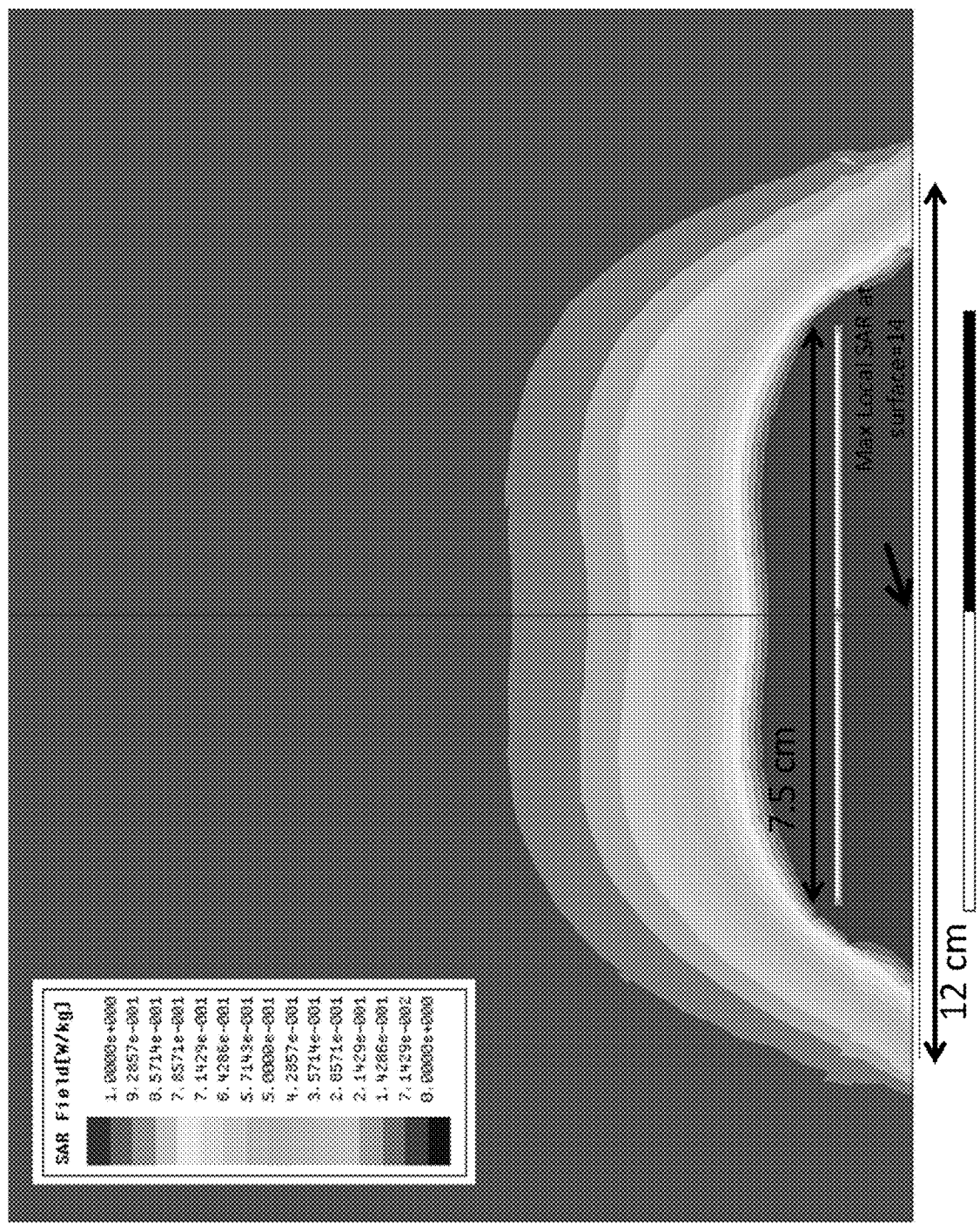
FIGS. 6A-6B show example radiation patterns of the wide dipole antenna assembly of FIGS. 4A-4B.
Figure 6B:
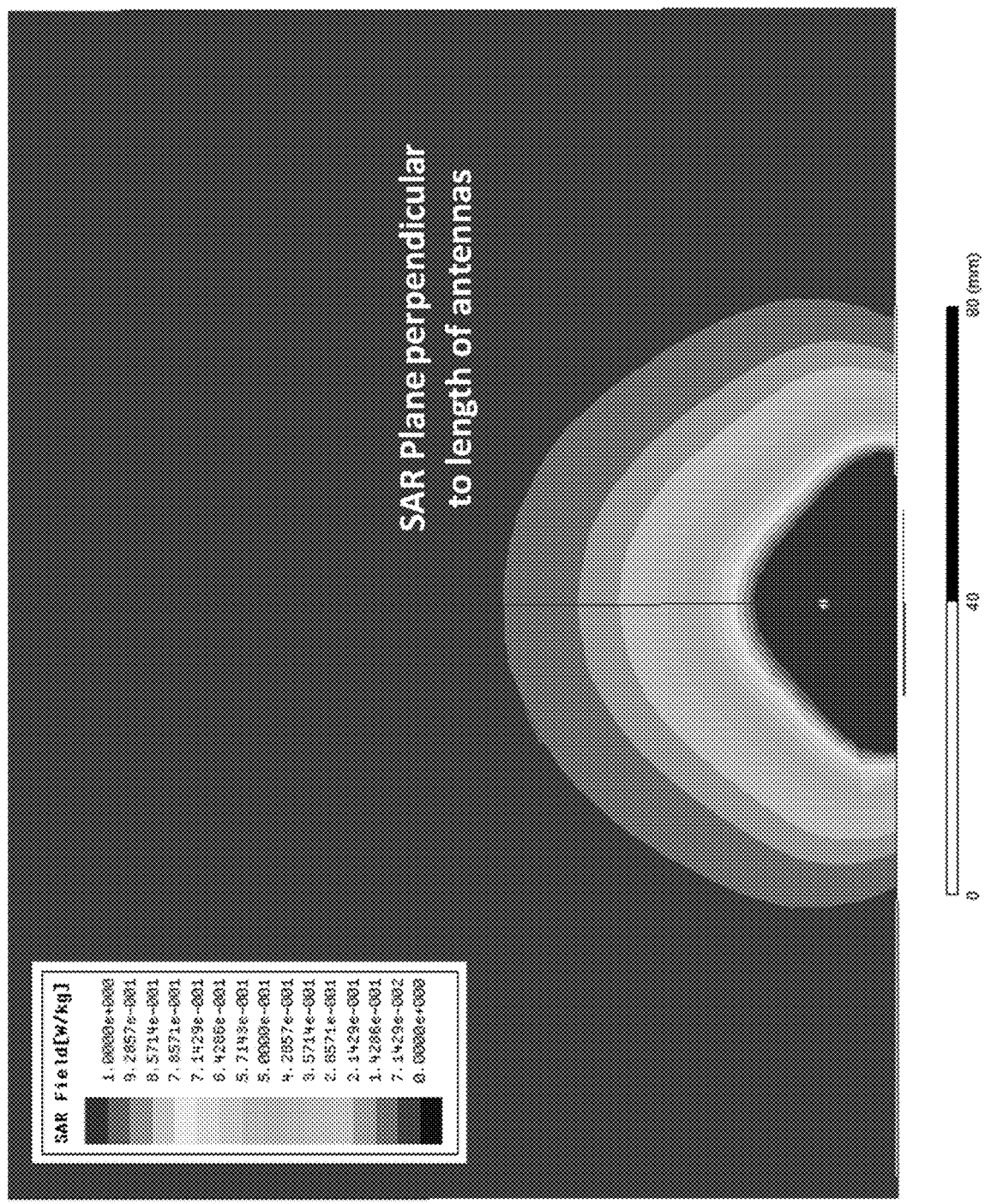

FIG. 6A-6B shows an example radiation patterns of the wide dipole antenna assembly. FIG. 6A shows the specific absorption rate (SAR) field pattern in a plane parallel to the length direction of wide dipole antenna assembly 400 for an average input power of 0.2 W and at 915 MHz. FIG. 6B shows the same specific absorption rate (SAR) field pattern in a plane perpendicular to the length direction of wide dipole antenna assembly 400 for an average input power of 0.2 W and at 915 MHz. In this example, the radiation patterns demonstrate that the field coverage extends sufficiently into the human body at various tissue depths with less than 25% reduction in field strength.

Figure 7A:
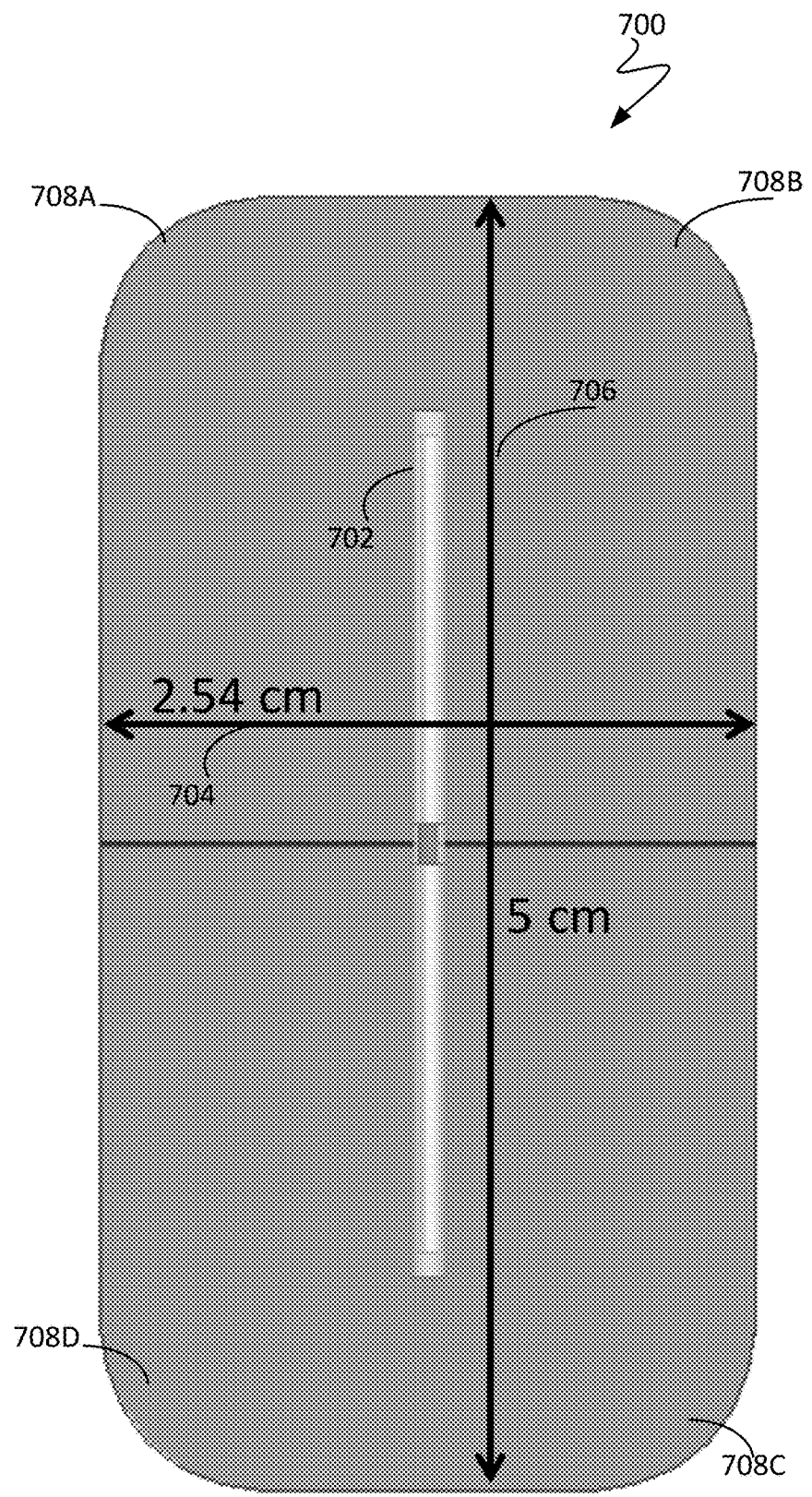
FIGS. 7A-7B show an example of a transmitting antenna configured as a wide dipole antenna assembly for operation at 2.4 GHz.
Figure 7B:
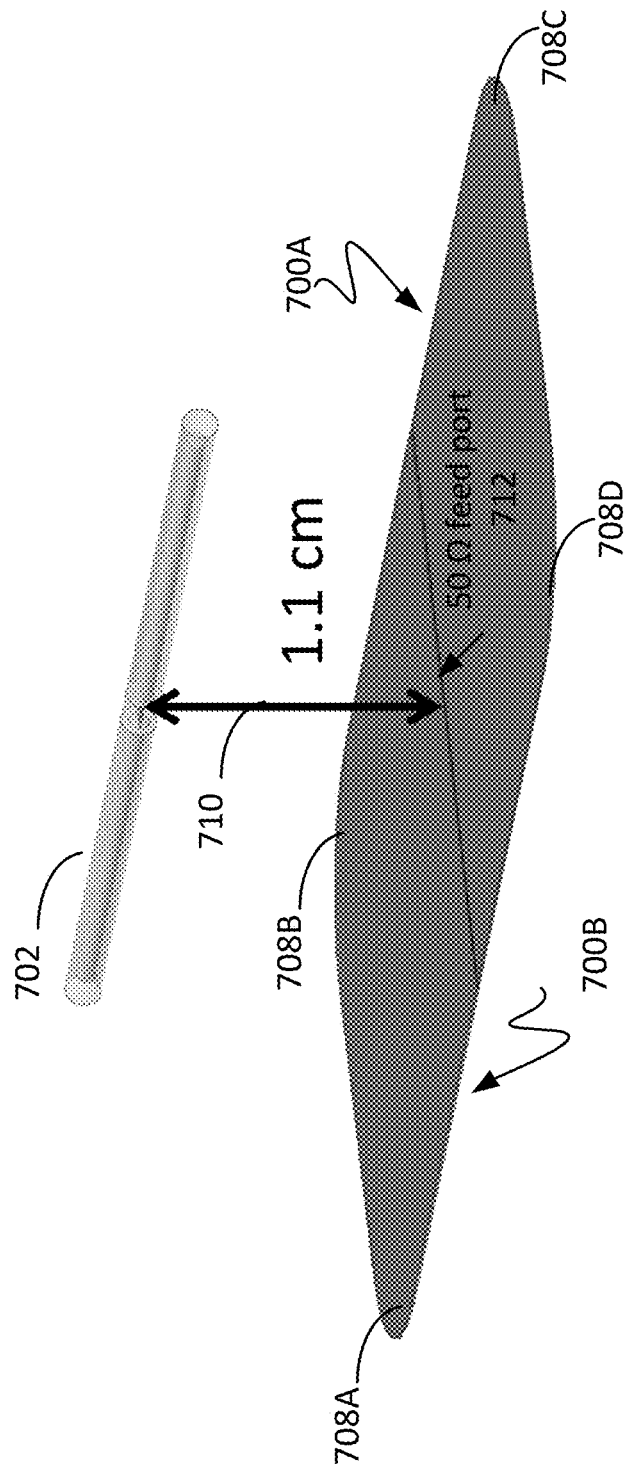

FIGS. 7A-7B shows an example of a transmitting antenna configured as a wide dipole antenna assembly 700 for operation at 2.4 GHz. FIG. 7A depicts a top view of the wide dipole antenna assembly 700, which has length in the range of 4 cm to 20 cm, a width 404 of 1 cm to 5 cm and four rounded corners or fillets. The particular example shown has a length 706 of 5 cm, a width 704 of 2.54 cm and four rounded fillets 708A to 708D, each rounded with a radius of 6.35 mm. The rounding may contribute to patient safety in that the round corners mitigate accidental injury due to sharp corners. As shown in FIG. 7B, wide dipole antenna assembly 700 includes an inward surface 700A to radiate EM energy towards the implanted stimulator device underneath the skin. Inward surface 700A may include signal metal layer. Inward surface 700A may be placed in proximity of the skin surface of a patient. The placement may be without gel coupling between the skin surface and the signal metal layer. Wide dipole antenna assembly 700 also includes an outward surface 700B which may be placed to face away from the skin. Outward surface 700B may provide protection against mechanical wear and tear. FIG. 7B further shows 50Ω feed port 712, for connecting wide dipole antenna assembly 700 to, for example, a microwave field stimulator (MFS) device. This 50Ω feed port 712 may be along the midline of the outward surface 700B. By way of example, BNC (Bonet Neill-Concelman) or SMC (SubMiniature version A) type connectors can be used to connect 50Ω feed port 712 to an MFS device through a co-axial cable.

FIGS. 7A and 7B also show receiving dipole 702 relative to the wide dipole antenna assembly 700. As illustrated, wide dipole patch antenna assembly 700 can be located 1.1 cm (710) from the receiving antenna 702. Wide dipole antenna assembly 700 radiates EM energy into the human body via the two ends along a longitudinal axis of metal layer. In particular, the wide dipole antenna assembly 700 has one end formed by corners 708A and 708B, and another end formed by corners 708C and 708D. The two ends may form a dipole configuration capable of transmitting electromagnetic waves linearly polarized along the direction of the two ends. When coupling to the receiving dipole antenna 702, this linear polarization of antenna assembly is aligned with the long axis of receiving dipole antenna 702. In some configurations, the metal layer is as small as 20 to 200 μm in thickness.

Figure 8:
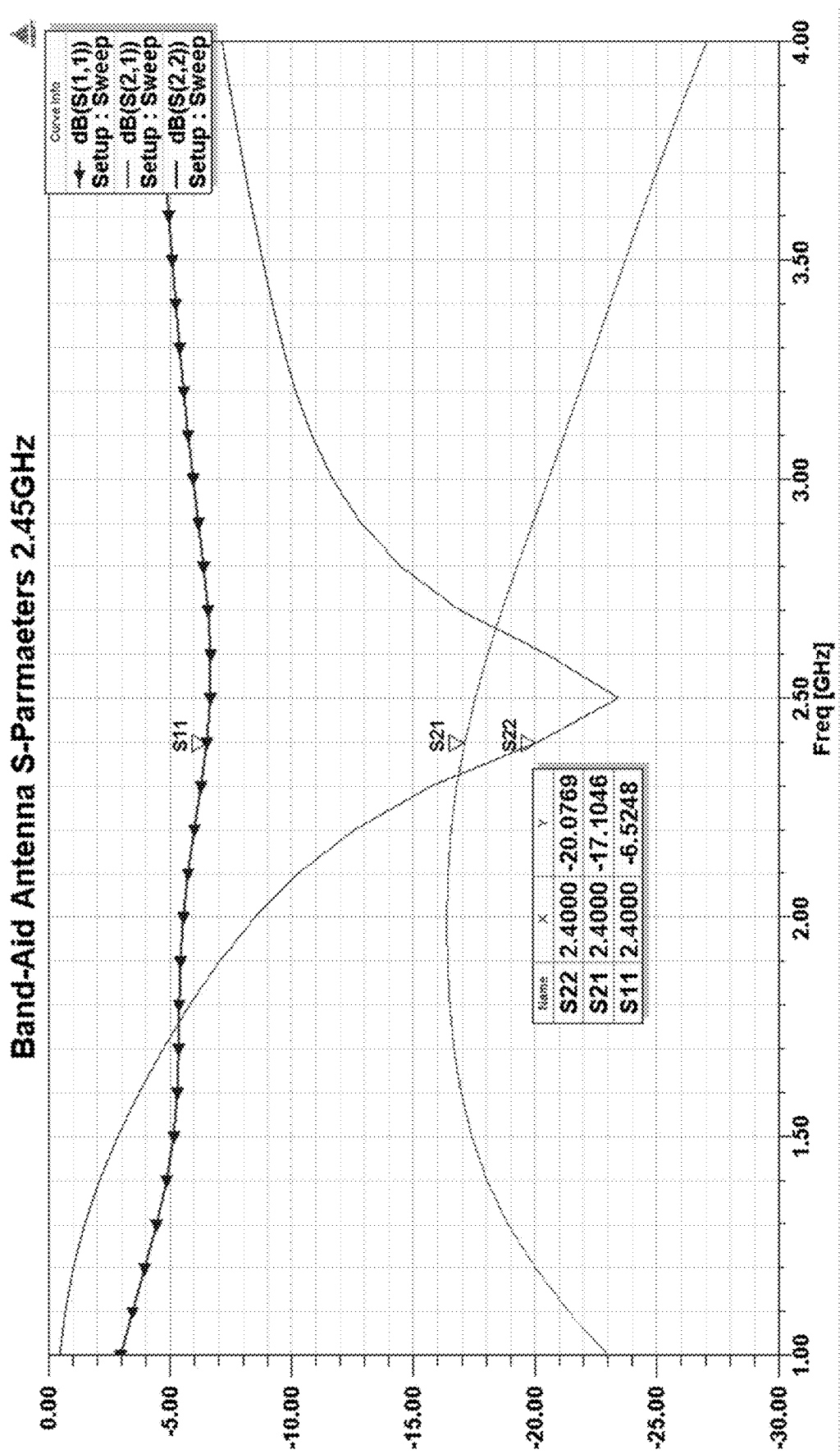
FIG. 8 shows S-parameter results of the wide dipole antenna assembly of FIGS. 7A-7B.

FIG. 8 shows S-parameter results of the wide dipole antenna assembly. Here, the S11 parameter (input port voltage reflection coefficient) and S22 parameter (output port voltage reflection coefficient) both have notches at the operating frequency of 2.4 GHz. Moreover, the S22 parameter is about 17 dB or so lower than the S11 parameter. These resonance performances are achieved without compromising the S21 parameter, which is the forward voltage gain. Notably, the S11 parameter indicates a reflection ratio of at least 6 dB at the operating frequency and, in particular, more than 6.5 dB. The antenna assembly 700 may be configured such that the reflection ratio of at least 6 dB at the operating frequency of the antenna assembly is maintained when the antenna assembly is positioned between zero to 2 centimeters, or more particularly, between zero to 1 centimeter, away from the patient's skin. That is, the antenna assembly 700 may be configured such that the S11 parameter notch at the operating frequency is wide enough that the S11 parameter remains below −6 dB as the antenna assembly 700 is positioned between 0 to 2 centimeters, or more particularly, between zero to 1 centimeter, away from the patient's skin.

FIG. 9 shows example radiation patterns of the wide dipole antenna assembly. In particular, FIG. 9 shows the specific absorption rate (SAR) field pattern in a plane parallel to the length direction of wide dipole antenna assembly 700 for an average input power of 0.2 W and at 2.4 GHz. The specific absorption rate (SAR) field pattern in the plane perpendicular to the length direction of wide dipole antenna assembly 700 has similar pattern. Here in this example, the radiation patterns demonstrate that the field coverage extends sufficiently into the human body at various tissue depths with less than 25% reduction in field strength.

Figure 10A:
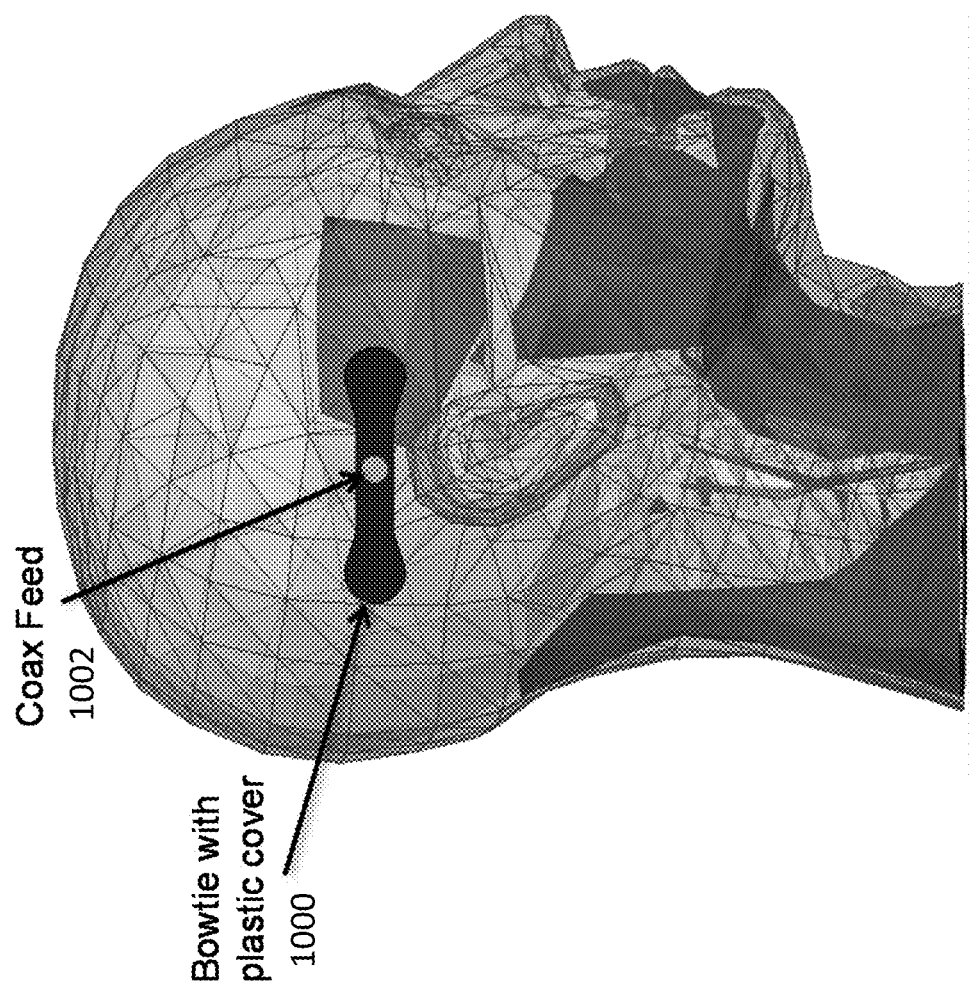
FIGS. 10A-10C show an example of a transmitting antenna configured as a bowtie antenna assembly.
Figure 10B:
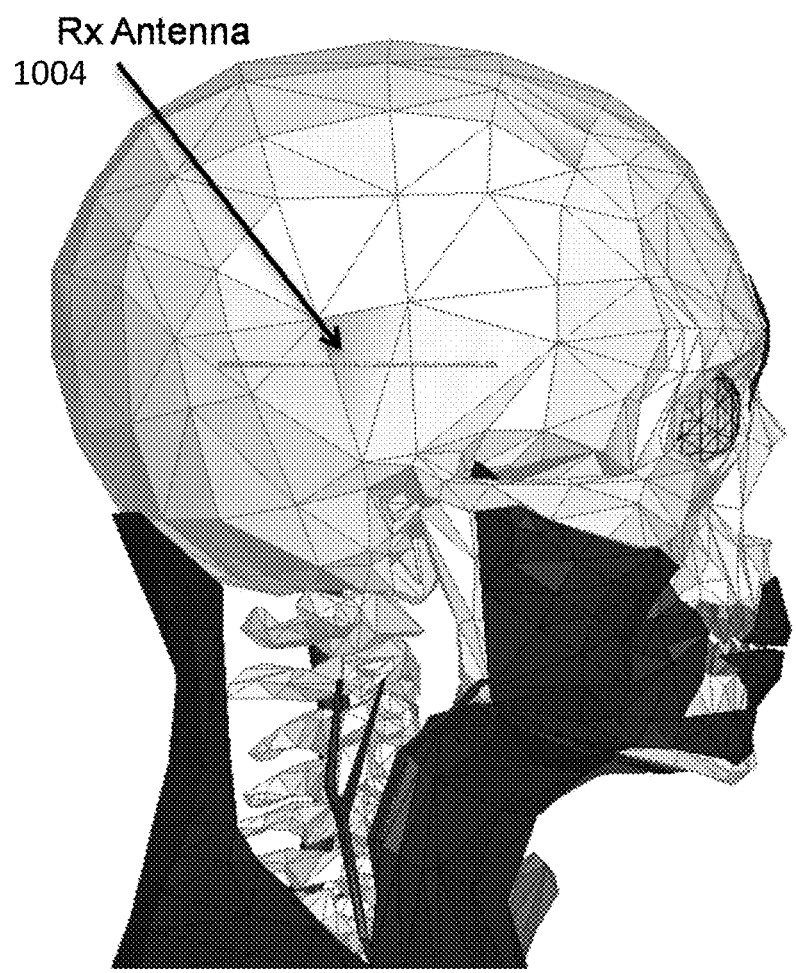
Figure 10C:
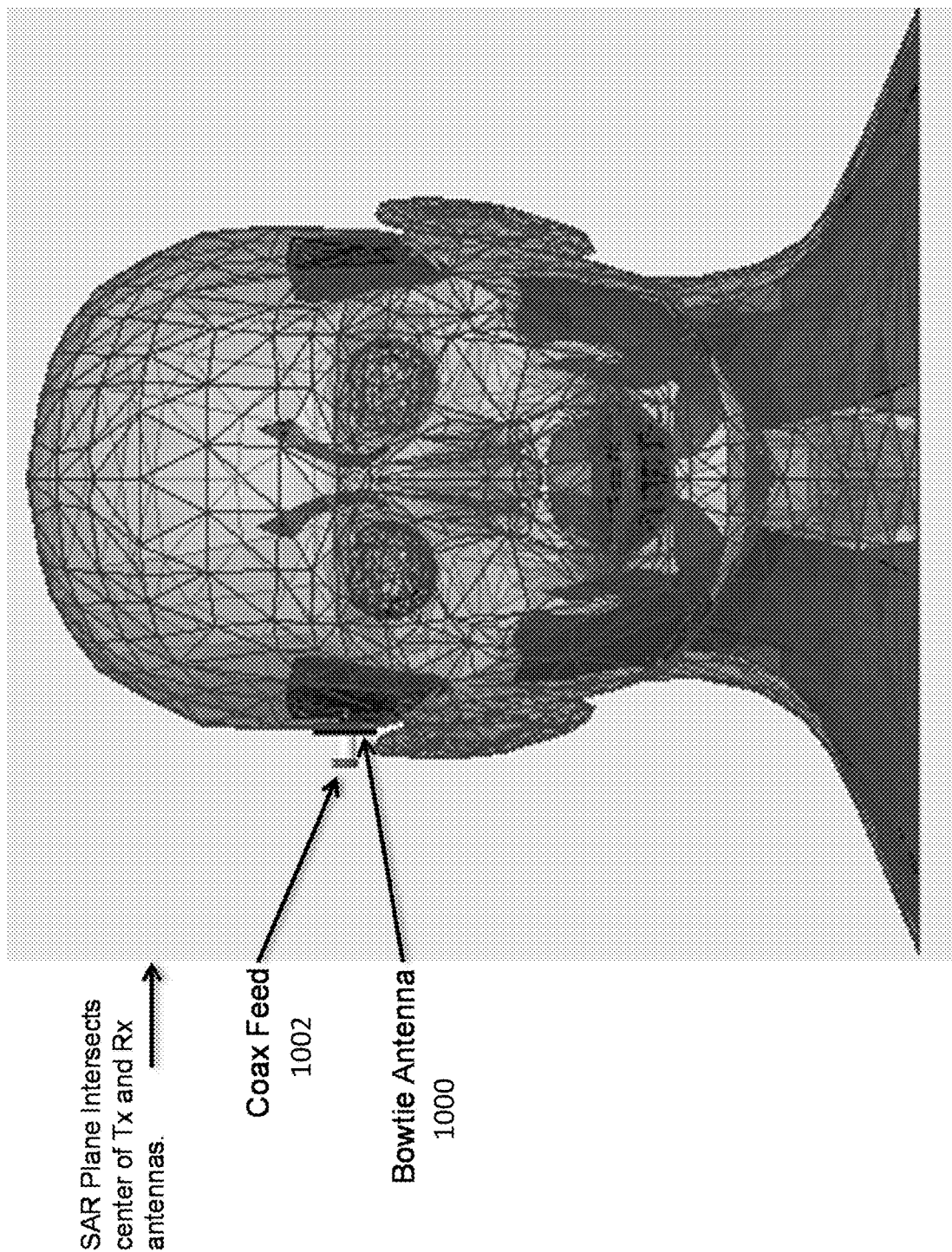

FIGS. 10A-10C show an example of a transmitting antenna configured as a bowtie antenna assembly 1000. For context, the illustrations in FIGS. 10A-10C show the mesh grid of a finite element model used in simulation experiments to investigate performance of bowtie antenna assembly 1000. In particular, FIG. 10A shows an example bowtie antenna assembly 1000 with a coax feed 1002 for a coax connection to a controller device such as a microwave field stimulator. The coax feed generally assumes a 50Ω load. The bowtie antenna assembly 1000, for example, is placed above the ear for radiating electromagnetic (EM) energy through the skin and into receiving antenna 1004 implanted just under the skin, as illustrated in FIG. 10B. The simulation incorporates model equations into the high frequency structural simulator to investigate the process of coupling EM energy from bowtie antenna assembly 1000 outside the skin to receiving antenna 1006 implanted at the skull outer surface. The simulation results demonstrated below are presented in the coronal plane that intersects center of the transmitting antenna 1000 and receiving antenna 1006.

Figure 11A:
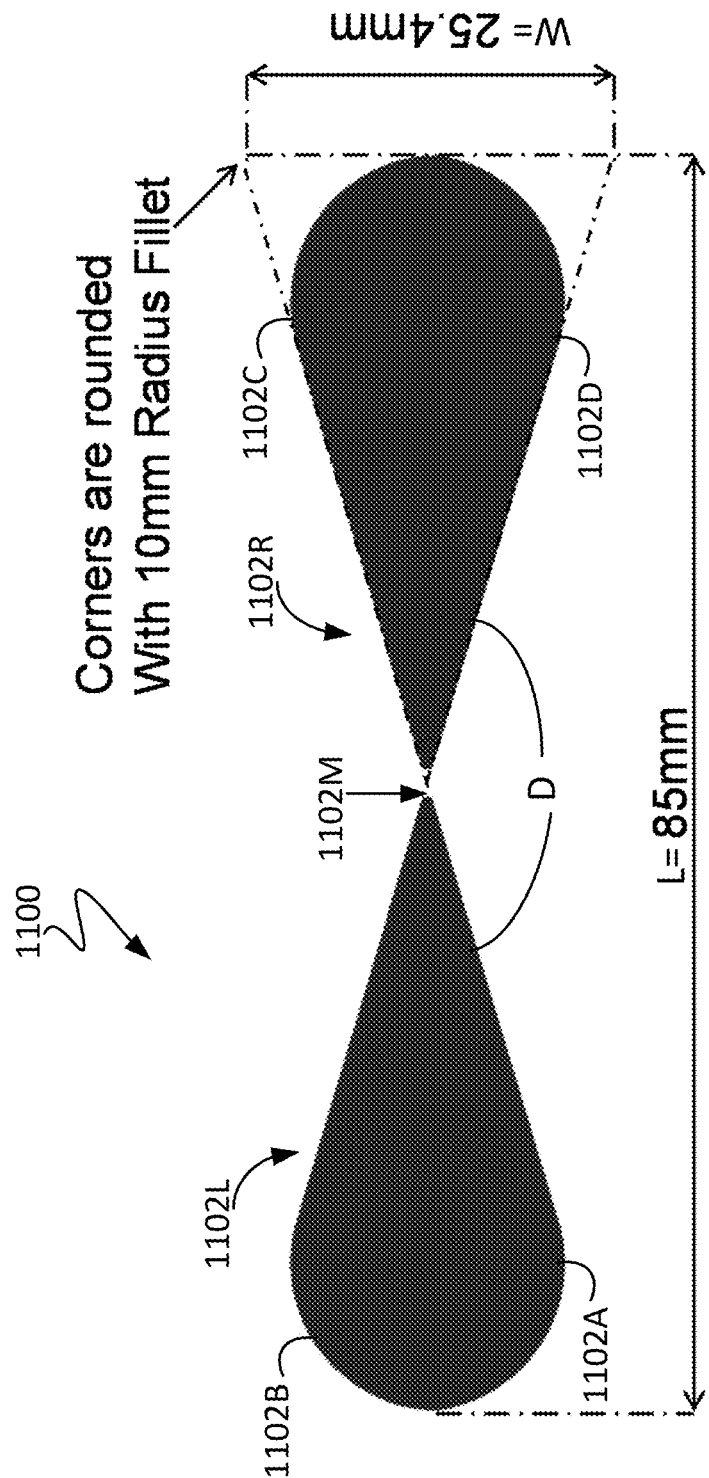
FIGS. 11A-11B show an example of a bowtie antenna assembly and the corresponding S-parameter.

As an initial matter, FIG. 11A shows the dimensions of the example bowtie antenna assembly 1100 as used in the stimulation investigations. Bowtie antenna assembly 1100 may generally include signal metal layer and a feed port, as discussed above in association with FIG. 3B. The bowtie antenna assembly 1100 includes two leaves, namely 1102L and 1102R, each of which has a width W at the widest point of 25.4 mm. The combined length L of leaves 1100L and 1100 R is 85 mm. The two leaves 1102L and 1102R form an angle of D. Here, the bowtie antenna assembly 1100 functions like a dipole transmitting antenna and the geometrical parameters of L, W, and D can determine the resonance behavior of bowtie antenna assembly 1100. During operation, the two leaves of bowtie antenna assembly 1100 may respectively function as a signal arm and a ground arm at any given time. The long axis of the two-leaf structure determines the direction of the linear polarization. As illustrated, leaf 1102L includes rounded fillets 1102A and 1102B while leaf 1100R includes rounded fillets 1102C and 1102D. Rounded fillets 1102A to 1102B are rounded with a 10 mm radius. Further, the two leaves 1102L and 1102R converge at 1102M where a 50 Ω feed port can be located. In other words, the two leaves 1102L and 1102R adjoin at vertex 1100M. The feed port may connect bowtie antenna assembly 700 to, for example, a signal generator, such as RF pulse generator 106. By way of example, BNC (Bonet Neill-Concelman) or SMC (SubMiniature version A) type connectors can be used to connect 50 Ω feed port to an MFS device through a co-axial cable The bowtie antenna length can vary between 50 to 120 cm, or greater.

Figure 11B:
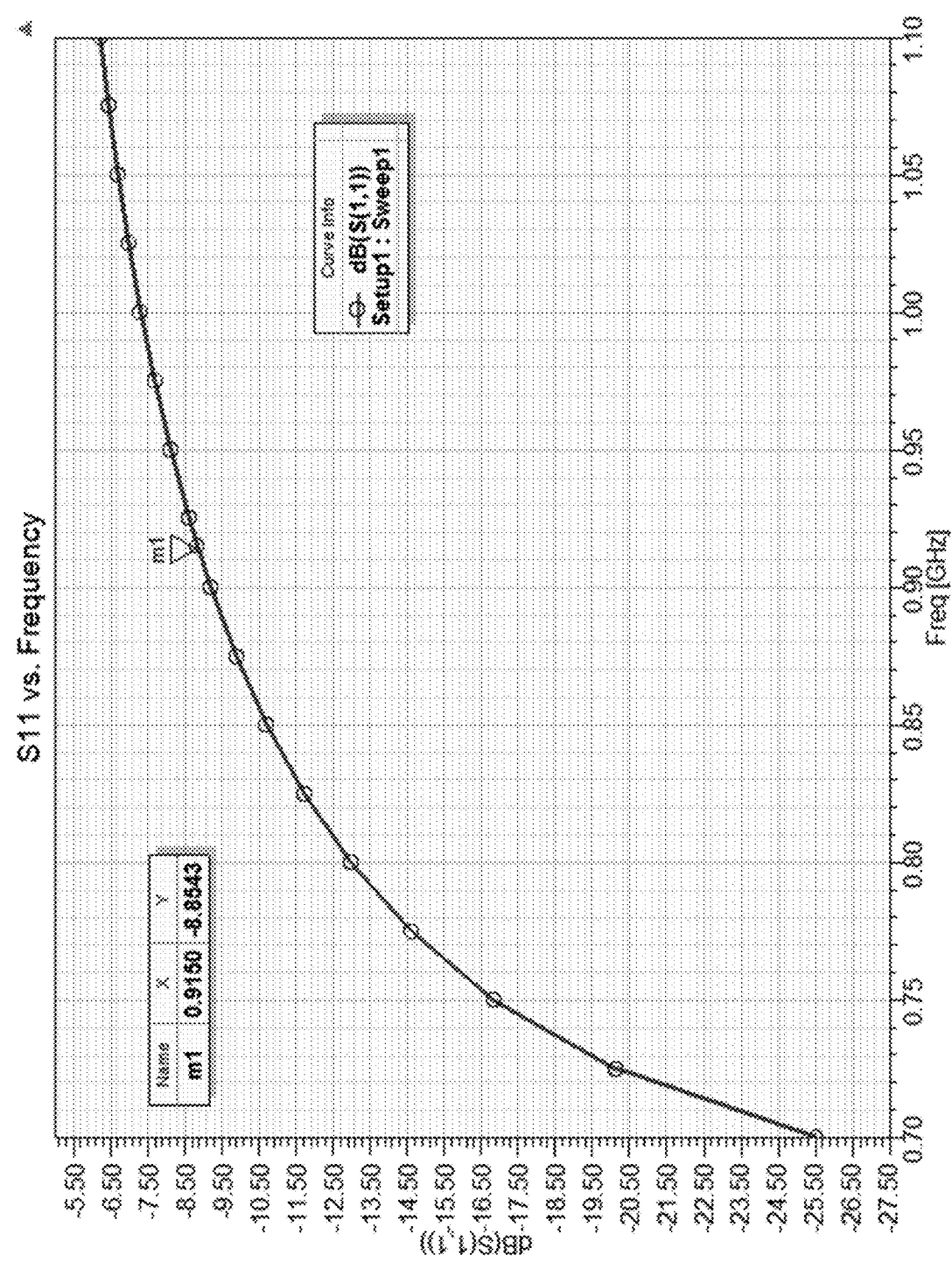

FIG. 11B shows the simulated S11 parameter (input port voltage reflection coefficient) for the bowtie antenna assembly 1100. There is an approximate 8.8 dB match at 915 MHz. Accordingly, the antenna assembly 1000 is configured to have a reflection ratio of at least 8 dB at the operating frequency. An 8.8 dB or more suppression means less than 14% of the transmitted energy may get reflected. In other words, more than 86% of the transmitted energy passes through. The antenna assembly 1000 may be configured such that the reflection ratio of at least 8 dB at the operating frequency of the antenna assembly is maintained when the antenna assembly is positioned between zero to 2 centimeters, or more particularly, between zero to 1 centimeter, away from the patient's skin. That is, the antenna assembly 1000 may be configured such that the S11 parameter notch at the operating frequency is wide enough that the S11 parameter remains below −8 dB as the antenna assembly 1000 is positioned between 0 to 2 centimeters, or more particularly, between zero to 1 centimeter, away from the patient's skin.

Figure 12A:
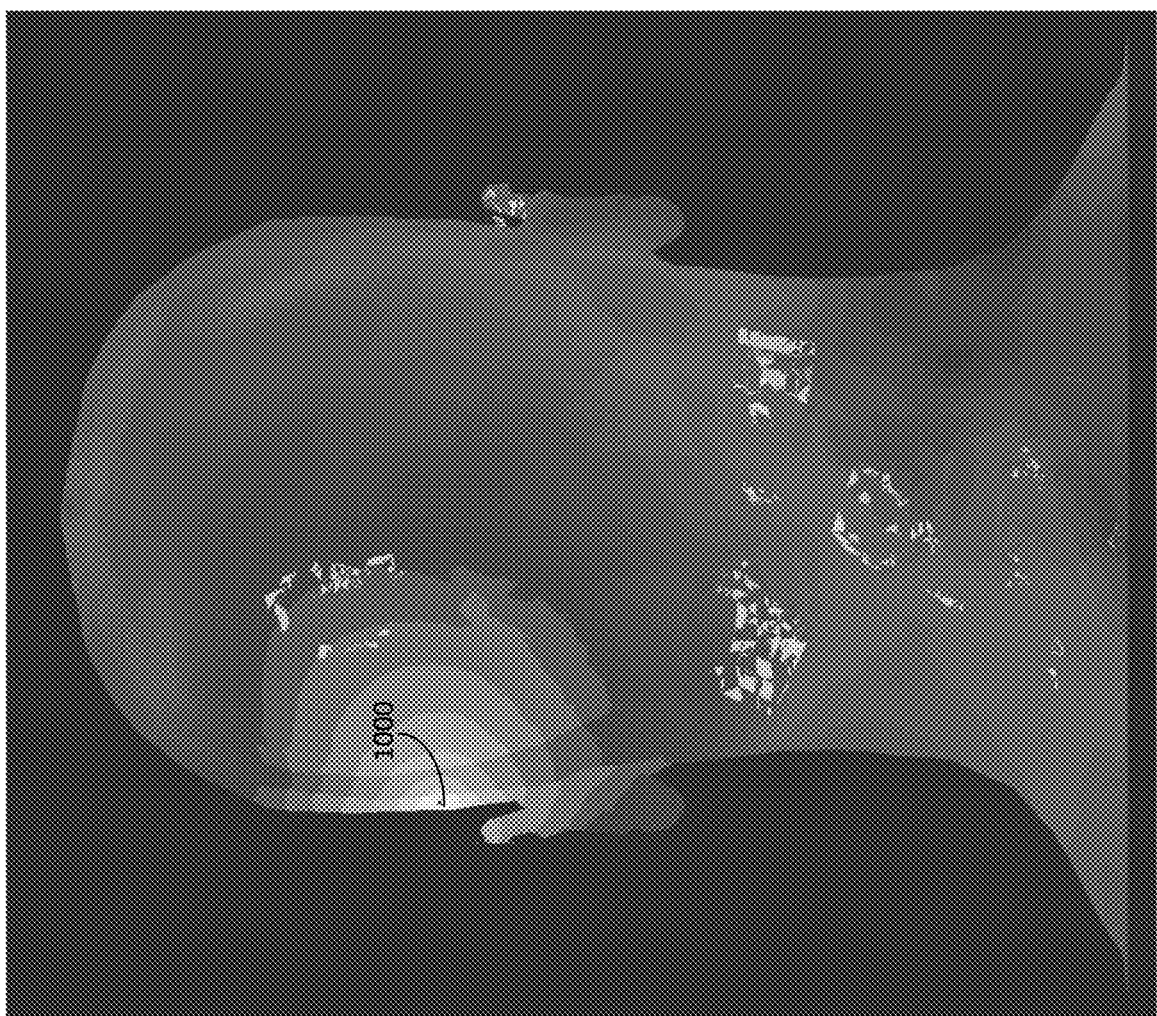
FIG. 12A shows an example of a radiation pattern of the bowtie antenna assembly of FIGS. 10A-10C in a sagittal view.

FIG. 12A shows an example of a radiation pattern from the bowtie antenna assembly of FIGS. 10A-10C in a sagittal view. Here, an example of the simulated specific absorption rate (SAR) resulting from the transcranial stimulation is presented at the bowtie antenna assembly 1000. The effect of a variety of parameters on the SAR patterns can be simulated. Therese parameters may generally include average input power, maximum peak power, and duty cycle. Average input power may be in the range of 20 mW to 80 mW. Peak power may be in the range of 2 to 4 W. Duty cycle may be in the range of 0.5% to 4%. Various SAR patterns demonstrate that the radiated EM field can penetrate through the skull for transcranial delivery of EM energy. Further, the penetration of the radiated EM field can be improved as the input power at the bowtie antenna assembly 1000 is ramped up from 20 mW to 80 mW.

Figure 12B:
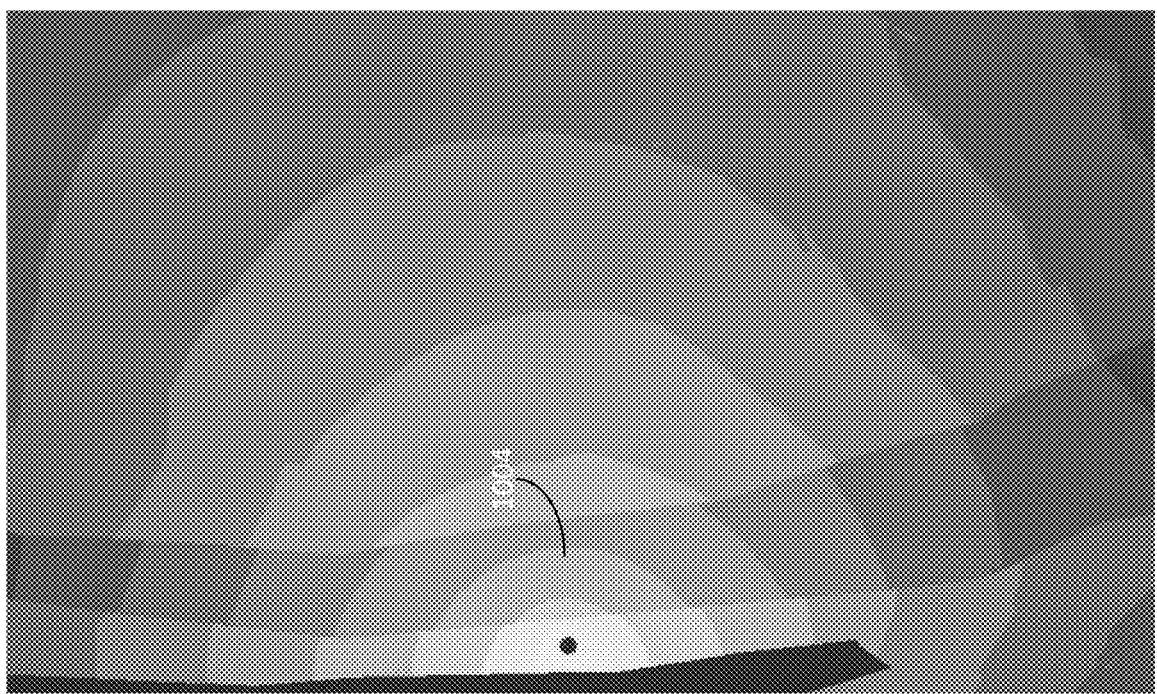
FIG. 12B shows an example radiation pattern from FIG. 12A in a zoomed view and superposed with the profile of the receiving antenna.

FIG. 12B shows the example radiation pattern of FIG. 12A in a zoomed view and superposed with the profile of the receiving antenna 1004, when the average input power at the bowtie antenna assembly 1000 is 80 mW. In this example, there is a SAR of 8 W/kg around the region occupied by the cross-sectional profile of the receiving antenna 1004. The area in which the SAR numbers are at the maximum allowable number may also be known as the hot spot. Here, the hot spot is about 4 mm under the skull, which generally coincides with the profile of the receiving antenna 1004.

Figure 13:
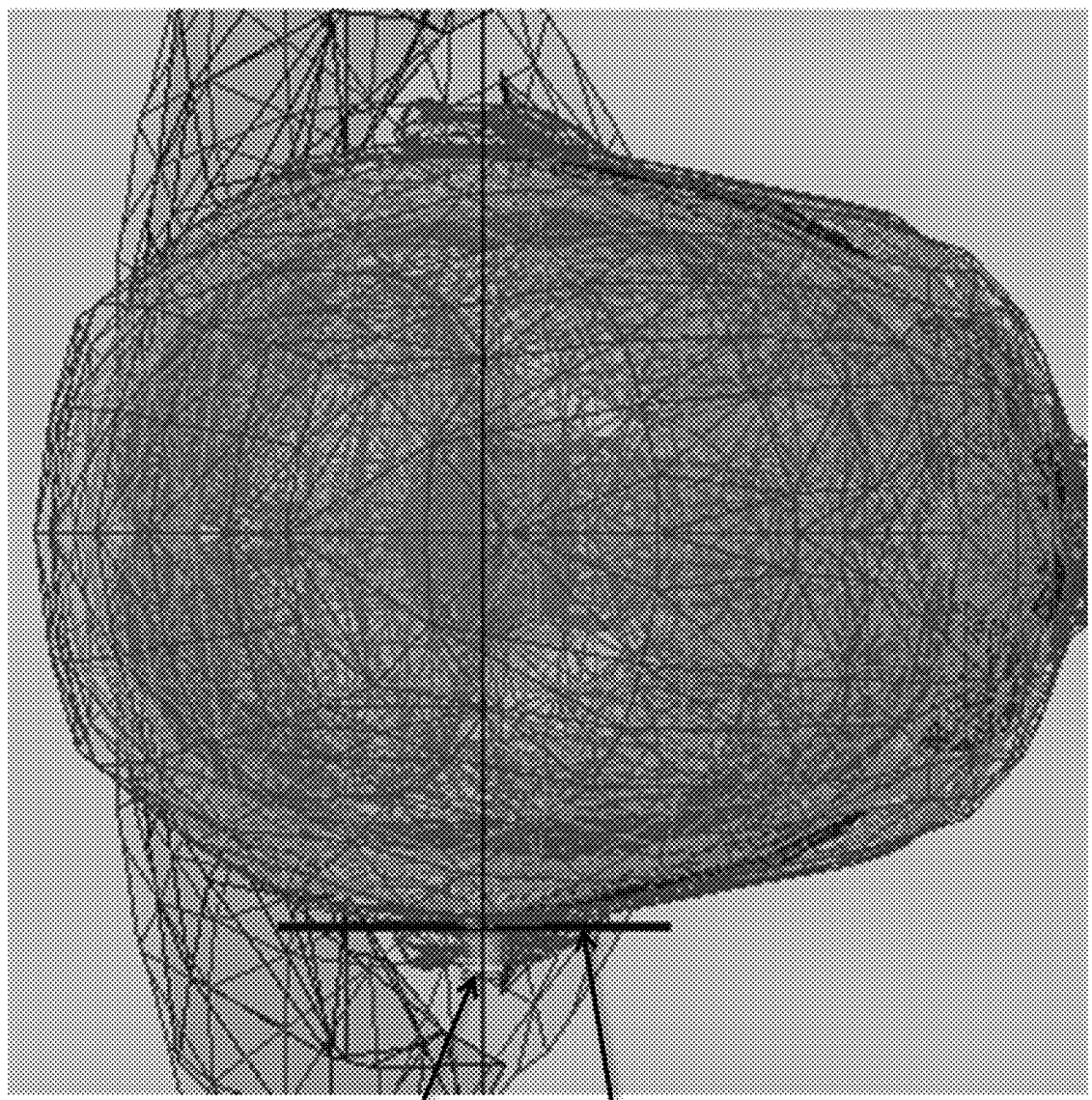
FIG. 13 shows the example bowtie antenna assembly in position for radiative treatment in an axial view.

FIG. 13 shows the example of the bowtie antenna assembly 1000 in position for radiative treatment in an axial view. As illustrated, the bowtie antenna assembly 1000 also includes a coaxial feed 1002 and configured to take on, for example, a 50 Ω load. Here, the illustration in FIG. 13 also shows the mesh grid of a finite element model used to in simulation experiments to investigate performance of bowtie antenna assembly 1000, as discussed above in association with FIGS. 10A-10C.

Figure 14A:
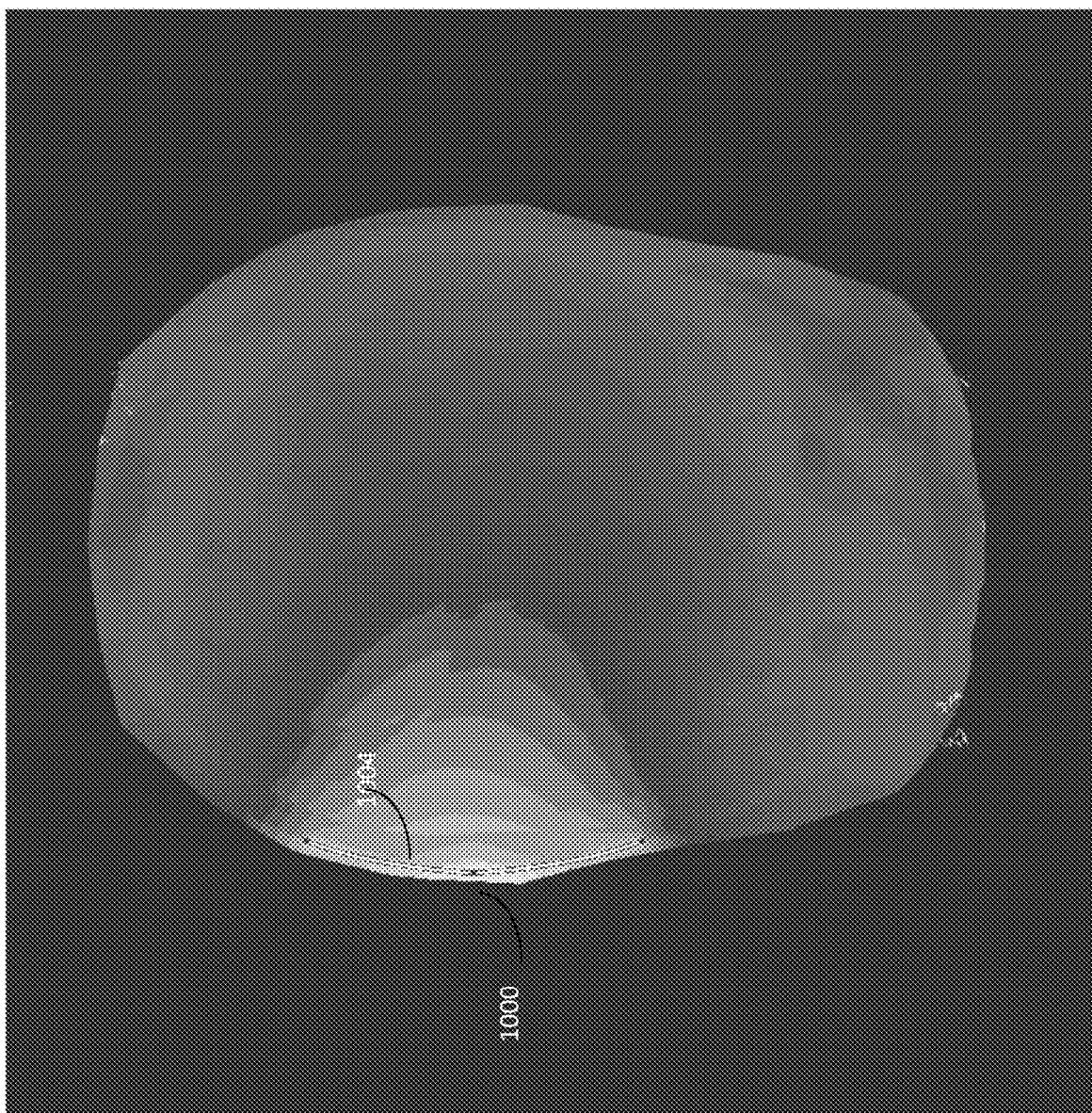
FIG. 14A shows an example of a radiation pattern of the bowtie antenna assembly of FIGS. 10A-10C in the axial view.

FIG. 14A shows an example of a radiation pattern from the bowtie antenna assembly of FIGS. 10A-10D in the axial view that captures the plane of the receiving antenna 1004. Here, the simulated specific absorption rate (SAR) resulting from the transcranial stimulation can be generated for various average input powers at the bowtie antenna assembly 1000, as discussed above in association with FIG. 12A. For example, the average input power can vary from 20 mW to 80 mW. The peak input power may be 2 W or greater, for example, from 2 W to 4 W. The duty cycle may change from 0.5% to 4%. Simulation results do demonstrate that the radiated EM field can penetrate through the skull for transcranial delivery of EM energy. The penetration of the radiated EM field can improve as the input power at the bowtie antenna assembly 1000 is ramped.

Figure 14B:
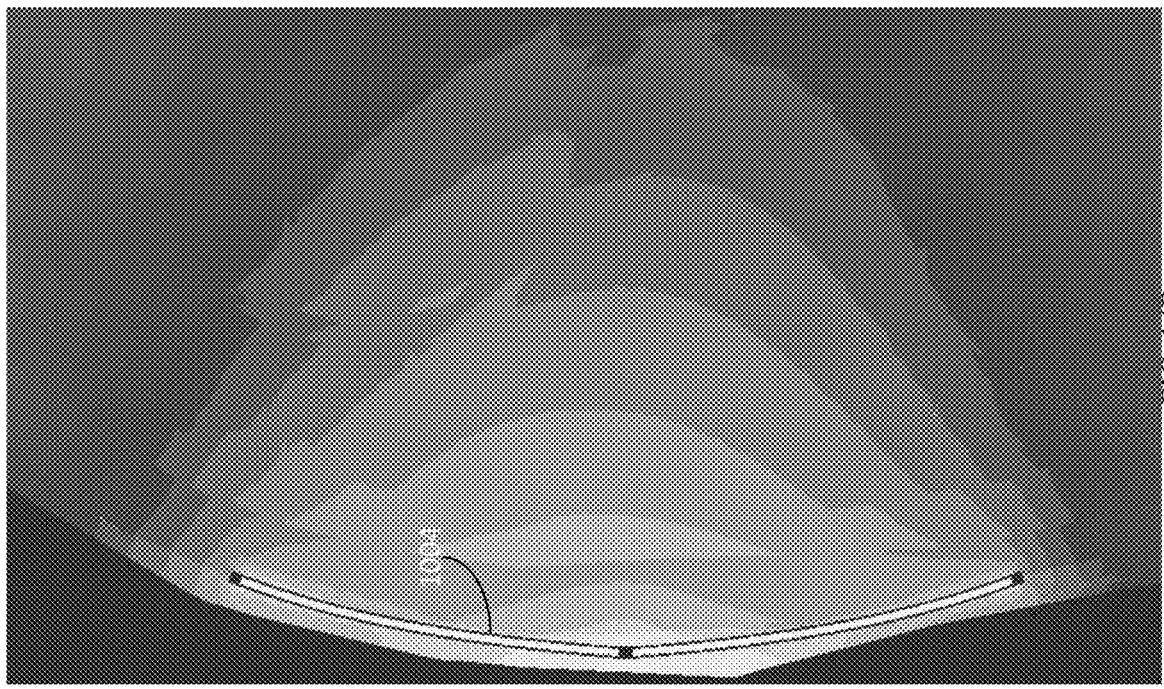
FIG. 14B shows the example of the radiation pattern of FIG. 14A in a zoomed view and superposed with the profile of the receiving antenna.

FIG. 14B shows an example of a radiation pattern from FIG. 14A in a zoomed view and superposed with the plane of the receiving antenna 1004, when the average input power at the bowtie antenna assembly 1000 is 80 mW. As illustrated, at 8 W/kg is generated around the region towards the middle of the plane of the receiving antenna 1004. The area in which the SAR numbers are at the maximum allowable number may also be known as the hot spot. Here, the hot spot is about 1.1 cm under the skull, which generally coincides with the plane of the receiving antenna 1004. In some instances, the bowtie configuration may be more likely to generate a higher concentration of electric field in the near field than a wide dipole configuration with comparable surface area. Here, higher concentration of electric filed may correspond to a larger amplitude in measured electric field strength both in terms of peak amplitude and mean amplitude. In this respect, the bowtie configuration may be more advantageous for emitting linearly polarized electromagnetic energy to a receiving dipole antenna.

A number of implementations have been described. Nevertheless, it will be understood that various modifications may be made. Accordingly, other implementations are within the scope of the following claims.

What is claimed is:
1. A system, comprising:
 a signal generator configured to generate an input signal containing electrical energy and stimulation pulse parameters; and
 a coil-less antenna assembly, comprising:
  a metal layer configured to emit a linearly polarized electric field to a receiving antenna implanted underneath a subject's skin such that the receiving antenna implanted underneath the subject's skin is non-inductively coupled to the antenna assembly and wirelessly receives the linearly polarized electric field emitted from the antenna assembly; and
  a feed port configured to connect the antenna assembly to the signal generator such that the antenna assembly receives an input signal from the signal generator and drives the metal layer using the input signal to emit the linearly polarized electric field to the receiving antenna,
  wherein the metal layer is a rectangular structure that is less than 200 μm in thickness, and
  wherein the antenna assembly operates with a reflection ratio of at least 6 dB, the reflection ratio corresponding to a ratio of a transmission power of the antenna assembly when driven by the input signal and a reflection power seen by the antenna assembly resulting from emission of the linearly polarized electric field to the receiving antenna implanted underneath the subject's skin.
2. The system of claim 1, wherein the metal layer includes four rounded fillets.

3. The system of claim 1, wherein the feed port is located on a midline of a surface of the rectangular structure.

4. The system of claim 1, wherein the antenna assembly is configured such that the antenna assembly can be bent up to 50 degrees while maintaining the reflection ratio of at least 6 dB.

5. The system of claim 1, wherein the antenna assembly is configured such that the reflection ratio of at least 6 dB is maintained regardless of a separation between the metal layer and a subject's skin.

6. The system of claim 1, wherein the antenna assembly is configured such that the reflection ratio of at least 6 dB is maintained with an air gap between the metal layer and the subject's skin.

7. The system of claim 1, wherein the antenna assembly is configured to transcranially emit the linearly polarized electric field when the antenna assembly is worn as part of an earpiece.

8. The system of claim 1, wherein the antenna assembly is configured to operate with a quality factor (Q) no more than 9.

9. The system of claim 1, wherein the antenna assembly is configured to operate at a frequency between 300 MHz and 8 GHz.

10. The system of claim 1, wherein a long axis of the rectangular structure aligns with a direction of the linearly polarized electric field.

11. A coil-less antenna assembly comprising:
a metal layer configured to emit a linearly polarized electric field to a receiving antenna implanted underneath a subject's skin such that the receiving antenna implanted underneath the subject's skin is non-inductively coupled to the antenna assembly and wirelessly receives the linearly polarized electric field emitted from the antenna assembly; and
a feed port configured to connect the antenna assembly to a signal generator such that the antenna assembly receives an input signal from the signal generator and then drives the metal layer using the input signal to emit the linearly polarized electric field to the receiving antenna,
wherein the metal layer is a rectangular structure that is less than 200 um in thickness, and
wherein the antenna assembly operates with a reflection ratio of at least 6 dB, the reflection ratio corresponding to a ratio of a transmission power of the antenna assembly when driven by the input signal and a reflection power seen by the antenna assembly resulting from emission of the linearly polarized electric field to the receiving antenna implanted underneath a subject's skin.

12. The antenna assembly of claim 11, wherein the metal layer includes four rounded fillets.

13. The antenna assembly of claim 11, wherein the feed port is located on a midline of a surface of the rectangular structure.

14. The antenna assembly of claim 11, wherein the antenna assembly is configured such that the antenna assembly can be bent up to 50 degrees while maintaining the reflection ratio of at least 6 dB.

15. The antenna assembly of claim 11, wherein the antenna assembly is configured such that the reflection ratio of at least 6 dB is maintained regardless of a separation between the metal layer and a subject's skin.

16. The antenna assembly of claim 11, wherein the antenna assembly is configured such that the reflection ratio of at least 6 dB is maintained with an air gap between the metal layer and the subject's skin.

17. The antenna assembly of claim 11, wherein the antenna assembly is configured to transcranially emit the linearly polarized electric field when the antenna assembly is worn as part of an earpiece.

18. The antenna assembly of claim 11, wherein the antenna assembly is configured to operate with a quality factor (Q) no more than 9.

19. The antenna assembly of claim 11, wherein the antenna assembly is configured to operate at a frequency between 300 MHz and 8 GHz.

20. The antenna assembly of claim 11, wherein a long axis of the rectangular structure aligns with a direction of the linearly polarized electric field.

* * * * *